United States Patent [19]

Barlow et al.

[11] 4,150,564
[45] Apr. 24, 1979

[54] OSMOMETER FOR COLLOID OSMOMETRY

[75] Inventors: Wayne K. Barlow; Howard G. Schimmelpfennig, both of Logan, Utah

[73] Assignee: Wescor, Inc., Logan, Utah

[21] Appl. No.: 895,111

[22] Filed: Apr. 10, 1978

[51] Int. Cl.$^2$ ............................................. G01N 13/04
[52] U.S. Cl. .................................................. 73/64.3
[58] Field of Search ...................................... 73/64.3

[56] References Cited

U.S. PATENT DOCUMENTS 3,195,346 7/1965 Ehrmantraut et al. ............... 73/64.3

FOREIGN PATENT DOCUMENTS 956,360 1/1957 Fed. Rep. of Germany ............. 73/64.3
1,907,811 8/1970 Fed. Rep. of Germany ............. 73/64.3

OTHER PUBLICATIONS

Collings et al., *A Diaphragm Cell for Diffusion Measurements in Liquids Under Pressure*, in J. Phys. E. Sci. Instr., 4(12): pp. 1019-1024, Dec. 1971.

Primary Examiner—Richard C. Queisser
Assistant Examiner—Joseph W. Roskos
Attorney, Agent, or Firm—Mallinckrodt & Mallinckrodt

[57] ABSTRACT

Instruments for use by medical laboratories to measure oncotic (colloid osmotic) pressure of blood for determining the risk of pulmonary edema are improved by the provision in the sensing heads thereof of a sinuous, preferably spiral, elongate, sample chamber facing one side of the usual osmotic membrane, whose other side faces a similar reference chamber for saline solution. The membrane is preferably pre-mounted in a ring holder, which merely slips into place within a receiving recess of the sensing head, and a special waste collection system is provided for receiving liquid flushed from the sample chamber between individual uses of the device. Such waste collection system comprises a drainage receptacle which constantly maintains a constant depth pool of the drained liquid about the discharge end of the drain tube that leads from the sample chamber, so as to maintain a constant end effect for such drain tube.

6 Claims, 7 Drawing Figures

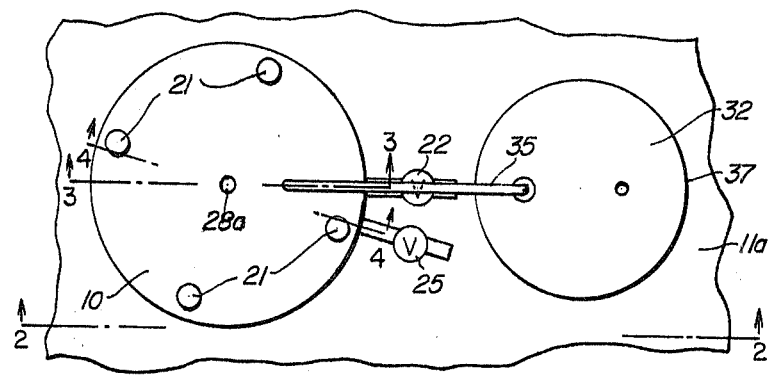
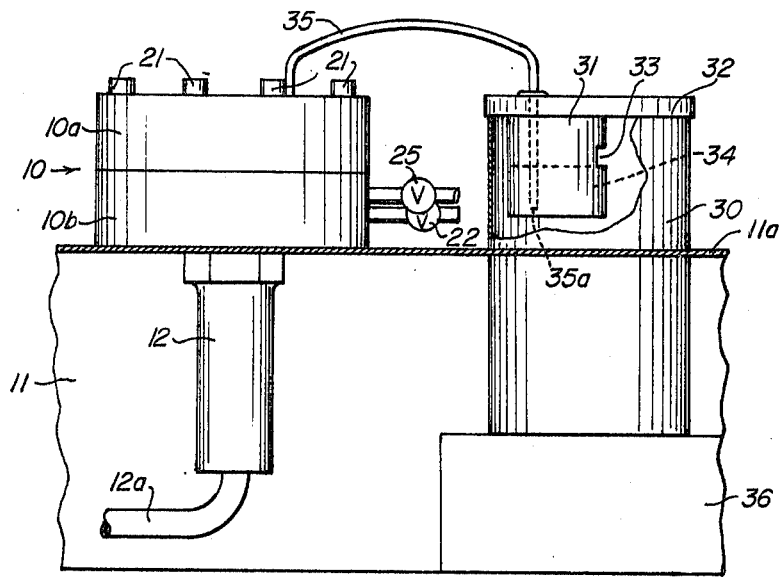
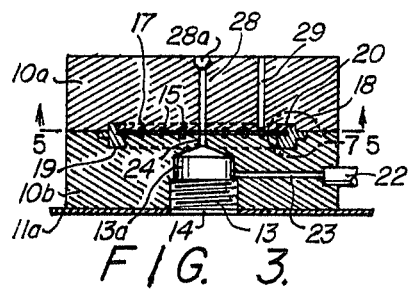

OSMOMETER FOR COLLOID OSMOMETRY

BACKGROUND OF THE INVENTION

Field: The invention is in the field of colloid osmometers, sometimes referred to as oncometers, for measuring oncotic or colloid osmotic pressures, e.g. of blood by medical laboratories to determine the presence of pulmonary edema that could cause heart failure.

State of the Art: The measurement of oncotic or colloid osmotic pressures of solutions of substances having high molecular weights, e.g. of blood proteins constituting colloids in colloidal blood solutions such as blood plasma or serum, and instruments for accomplishing same have been described by Theodore R. Reiff and Marvin J. Yiengst in a paper entitled "A Rapid Automatic Semimicro Colloid Osmometer", published in the Journal of Laboratory and Clinical Medicine, Vol. 53, No. 2, pp. 291–298, Feb. 1959, and by Max Harry Weil et al. in a paper entitled "routine Plasma Colloid Osmotic Pressure Measurements", published in Critical Care Medicine, Vol. 2, No. 5, pp. 229–234, September-October 1974. Bisera et al. U.S. Pat. No. 4,028,931, issued June 14, 1977, entitled "Osmotic Pressure Sensing Head" discloses an improved sensing head for such an instrument. These all employ a sample chamber and a corresponding reference chamber that confront each other through a spot-like area of an intervening osmotic membrane. The patented improvement directs the incoming flow of sample solution onto the membrane at an angle such that debris is flushed from the corresponding surface of the membrane.

For many years there has been on the market a similar instrument produced by David E. Burge, doing business as Wescan Instruments, Santa Clara, Calif. There, however, the sample chamber and corresponding reference chambers are narrow and elongate and extend over a zigzag path of considerable length having numerous abrupt, right-angle turns. Solution is introduced at one end of the path in each chamber and withdrawn at the other end of the path.

Objectives: In the making of the present invention, it was a principal objective to provide considerable contact area for the sample and reference solutions with the osmotic membrane, while minimizing pressure response time. Further objectives were to provide for good flushing action within the sample chamber during cleaning thereof following each use of the instrument, to insure accuracy of results in the making of measurements, and to provide for easy replacement of the membrane when necessary.

SUMMARY OF THE INVENTION

For accomplishing the objectives of the invention, the sample and reference chambers of the sensing head of the instrument are made long and narrow, as in the Burge instrument, but, unlike that instrument, the path is sinuous with gentle curves as in a spiral. Accuracy of pressure measurements are assured with a waste collection system whose drain tube extends from the discharge end of the sample chamber into a waste receptacle adapted to constantly maintain a constant depth pool of the waste solution about the discharge end of the drain tube to provide a constant end effect for such drain tube. Easy replacement of the osmotic membrane when necessary is provided for by pre-mounting the membrane within a rigid holding ring adapted to be slipped into place within a receiving recess in the sensing head.

THE DRAWINGS

An embodiment representing what is presently contemplated as the best mode of carrying out the invention in actual practice is illustrated in the accompanying drawing in which:

FIG. 1, is a fragmentary top plan view of a colloid osmometer incorporating the invention;

FIG. 2, a vertical section taken on the line 2—2 of FIG. 1;

FIG. 3, a vertical section taken on the line 3—3 of FIG. 1;

FIG. 4, a similar vertical section taken on the line 4—4 of FIG. 1;

FIG. 5, a horizontal section taken on the line 5–5 of FIG. 3;

FIG. 6, a similar horizontal section taken on the line 6–6 of FIG. 4; and

FIG. 7, an enlarged view of that portion of FIG. 3 included within line 7.

DETAILED DESCRIPTION OF THE ILLUSTRATED EMBODIMENT

In the form illustrated, the colloid osmometer comprises a sensing head 10 having an upper section 10a and a lower section 10b. Such sensing head is mounted in a cabinet 11 and rests on a horizontal wall 11a therein. It may be made of a non-corroding metal such as stainless steel or a metal such as brass with critical surfaces plated with a non-corroding metal such as gold or chromium, or a rigid plastic material. It has a pressure transducer 12 of standard make connected thereto, as by threading into a receiving opening 13 thereof, FIGS. 3 and 4. An opening 14 is provided through wall 11a for this purpose.

As is customary, a sample chamber for receiving plasma or serum blood specimen withdrawn from a medical patient suspected of having pulmonary edema is provided in the lower face of the sensing head upper section 10a, and a reference chamber for the reception of a suitable reference liquid such as a saline solution is provided in the upper face of the sensing head lower section 10b. Also, as is customary, such sample and reference chambers are separated by an osmotic membrane.

In accordance with the present invention, these chambers are of corresponding, elongate sinuous formation free of abrupt bends. Thus, as illustrated, the sample chamber 15 is of spiral formation, and the reference chamber 16 is of corresponding spiral formation. Although other formations that are elongate, narrow, and sinuous, free of abrupt bends, may be employed, the illustrated spiral formation is preferred because of the considerable chamber area that can be provided with long sweeping curves and because flow of liquid therethrough is free and easy with practically no opportunity for hang-up or edy currents. In fact, flow is essentially laminar in character, as is desired.

The chambers open into each other along their lengths except for the interpositioning therebetween of an osmotic membrane 17.

A feature of the invention is the pre-mounting of membrane 17 in a rigid ring holder 18, which is quickly and easily slipped into a receiving recess 19 in sensing head lower section 10b. Ring holder 18 includes a membrane retaining ring 18a, FIG. 7, and is also received by a receiving recess 20 in sensing head upper section 10a. With the membrane and its ring holder in place in the upper face of sensing head lower section 10b, sensing head upper section 10a is placed thereover in face-to-face relationship therewith, as illustrated in FIGS. 3 and 4, and the two sensing head sections are secured together by elongate screws 21.

Saline solution is introduced into reference chamber 16, as by means of a standard syringe, through manually operated stopcock valve 22 communicating with a tubular flow passage 23 which intersects the upper portion 13a of opening 13. A tubular flow passage 24 connects opening 13a with the end 16a of chamber 16 at the center of the spiral.

A second stopcock valve 25 connects through tubular passages 26 and 27 with the outer end 16b of chamber 16 and provides for flow out of chamber 16 during the filling thereof until all air bubbles have been eliminated. When this is attained, both stopcocks 22 and 25 are closed.

Filling of sample chamber 15, first with a saline solution for calibration purposes and later with a blood specimen, is accomplished by the use of respective syringes which pass their contents through tubular passage 28 in sensing head upper section 10a which connects with the inner end 15a of chamber 15 at the center of the spiral. The discharge end of the syringe is placed in recess 28a for the purpose of introducing the contained liquid into passage 28. Liquid flowing through chamber 15 discharges from outer end 15b by way of tubular passage 29 until all air bubbles are eliminated from chamber 15.

A principal waste receptacle 30 is mounted in cabinet 11 as close as practical to sensing head 10 so that the drain path for liquid from tubular passage 29 will be as short as possible. A secondary waste receptacle 31 is incorporated in primary waste receptacle 30 advantageously by being secured to removable cover 32 for such primary waste receptacle 30. Secondary waste receptacle 31 has an overflow discharge opening 33 at a predetermined level which provides a constant pool of waste liquid 34 of constant depth. A drain tube 35 connects tubular passage 29 with secondary waste receptacle 31 and has its discharge end 35a submerged at a predetermined depth in pool 34. This provides a constant end effect for such drain tube so as to insure accurate pressure readings across osmotic membrane 17.

The height of the liquid in secondary waste rceptacle 31, and the depth therein to which drain tube 35 is inserted, is not critical. Small variations in these do not significantly affect the pressure readings. The importance of the pool of liquid is that it eliminates significant variations between readings taken when a drop of liquid remains on the end of a drain tube suspended in air and readings when no drop remains on such a tube, or variations due to differences in the size of a drop remaining at the end of the tube. These variations appear to be due to differences in surface tension at the end of the tube and resulting forces which are transmitted to the sample chamber.

Primary waste receptacle 30 is supported in cabinet 11 by a platform structure 36 and extends upwardly through a receiving opening 37, FIG. 1, in wall 11a. It is easily removed for emptying and replaced thereafter.

Oncotic pressure measurements are made in customary manner by pressure transducer 2 and interconnecting electronic circuitry of known type and arrangement. Pressures sensed by transducer 12 are sent as measurement signals through an electrical cable 12a to the electronic circuitry used to translate such signals into useful read-out information, all in accordance with known practice in the art.

A series of samples for which readings are desired may be introduced into the sample chamber one after the other. The introduction of a sample into the chamber flushes the chamber of the prior sample. Because of the sinuous formation of the chamber and absence of abrupt bends, there is very little mixing of the various samples and effective readings of each sample may be obtained with minimum flushing and sample volume.

Whereas this invention is here illustrated and described with specific reference to an embodiment thereof presently contemplated as the best mode of carrying out such invention in actual practice, it is to be understood that various changes may be made in adapting the invention to different embodiments without departing from the broader inventive concepts disclosed herein and comprehended by the claims that follow.

We claim:

1. In a colloid osmometer having a sensing head provided with substantially coextensive sample and reference chambers separated by an osmotic membrane, the improvement comprising sample and reference chambers of corresponding, elongate, narrow, sinuous formation free of abrupt bends and having means for the supply of sample and reference solutions, respectively, at one set of ends, and means for the discharge of sample and reference solutions, respectively, at an opposite set of ends; and a waste collection system for liquid flushed from the sample chamber, said system comprising a waste receptacle adapted to constantly maintain a pool of waste liquid at constant depth, and a drain tube adapted to have one of its ends connected to the discharge end of the sample chamber and to have its other end submerged in said pool of waste solution.

2. The improvement set forth in claim 1 wherein the sample and reference chambers are of spiral formation.

3. The improvement set forth in claim 1. wherein the membrane is pre-mounted in a ring holder, and the sensing head is provided with a receiving recess for said ring holder surrounding the sample and reference chambers so that the membrane will fit between and separate said chambers when the ring holder is in place in its receiving recess.

4. The improvement set forth in claim 1, wherein the waste collection system comprises a primary waste receptacle having considerable storage capacity and a secondary waste receptacle mounted in the upper part of said primary waste receptacle and having relatively limited storage capacity, said secondary waste receptacle having an overflow discharge opening at a predetermined level whereby a pool of liquid is constantly maintained at constant depth, said drain tube being adapted to lead into and be submerged within said pool at predetermined depth.

5. In a colloid osmometer having a sensing head provided with substantially coextensive sample and reference chambers separated by an osmotic membrane, the improvement comprising a waste collection system for liquid flushed from the sample chamber, said system comprising a waste receptacle adapted to constantly maintain a pool of waste liquid at constant depth, and a drain tube adapted to have one of its ends connected to the discharge end of the sample chamber and to have its other end submerged in said pool of waste solution.

6. In a colloid osmometer having a sensing head comprising upper and lower sections adapted to fit together in face-to-face relationship and provided with substantially coextensive sample and reference chambers respectively separated by an osmotic membrane, the improvement wherein the membrane is pre-mounted in a ring holder, and the sensing head is provided with a receiving recess for said ring holder between said sections, surrounding the sample and reference chambers, and spaced inwardly from the periphery of said sensing head sections, so that the membrane will fit between and separate said chambers when the ring holder is in place in its receiving recess.

* * * * *